United States Patent [19]

Varma et al.

[11] 4,427,592
[45] Jan. 24, 1984

[54] ANDROSTENE-17-DITHIOKETALS

[75] Inventors: Ravi K. Varma, Belle Mead; Donald S. Karanewsky, East Windsor, both of N.J.

[73] Assignee: E. R. Squibb & Sons, Inc., Princeton, N.J.

[21] Appl. No.: 462,164

[22] Filed: Apr. 7, 1983

[51] Int. Cl.³ .............................................. C07J 1/00
[52] U.S. Cl. .......................... 260/397.45; 260/397.3; 260/397.5
[58] Field of Search .................... 260/397.45; 424/243

[56] References Cited

U.S. PATENT DOCUMENTS

| | | | |
|---|---|---|---|
| 4,018,774 | 4/1977 | Varma et al. | 260/239.55 R |
| 4,091,036 | 5/1978 | Varma | 260/397.45 |
| 4,094,840 | 6/1978 | Varma | 260/397.45 |
| 4,133,811 | 1/1979 | Varma | 260/397.45 |
| 4,146,538 | 3/1979 | Varma et al. | 260/397.45 |
| 4,164,504 | 8/1979 | Varma | 260/397.1 |
| 4,265,815 | 5/1981 | Varma | 260/397.45 |
| 4,361,559 | 11/1982 | Varma | 260/397.45 |

*Primary Examiner*—Elbert L. Roberts
*Attorney, Agent, or Firm*—Lawrence S. Levinson; Donald J. Barrack

[57] ABSTRACT

Topical antiinflammatory activity is exhibited by steroids having the formula

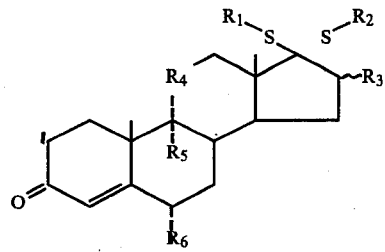

and the 1,2-dehydro, and 6,7-dehydro derivatives thereof, wherein one of $R_1$ and $R_2$ is alkyl, aryl, arylalkyl, or cycloalkyl, and the other is alkenyl, substituted alkenyl, alkynyl, substituted alkynyl, mono-, di- or trifluoroalkyl, cyanoalkyl, alkanoylalkyl or

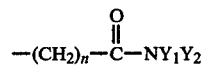

wherein n is 1, 2, 3 or 4 and $Y_1$ and $Y_2$ are the same or different and each is hydrogen or alkyl;

$R_3$ is hydrogen, hydroxy, alkoxy, aryloxy, oxo, methylene, alkylthio, arylthio, alkanoyl, alkanoyloxy, or fluorine;

$R_4$ is carbonyl, β-hydroxymethylene or β-acetyloxymethylene;

$R_5$ is hydrogen or halogen; and $R_6$ is hydrogen, methyl, hydroxy, alkanoyl, alkanoyloxy or halogen.

23 Claims, No Drawings

ANDROSTENE-17-DITHIOKETALS

RELATED APPLICATIONS

United States patent application Ser. No. 396,178, filed July 7, 1982, discloses androstene-17-dithioketals having the partial structural formula

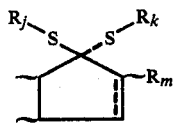

wherein one of $R_j$ and $R_k$ is alkyl, cycloalkyl, aryl, arylalkyl, or —$CH_2X$ wherein X is alkylthio, alkoxy, aroyloxy, alkanoyloxy or alkoxycarbonyl and the other is alkylthioalkyl, alkoxyalkyl, alkanoyloxyalkyl, aroyloxyalkyl, alkoxycarbonylalkyl, carboxyalkyl or arylalkyl; $R_m$ is hydrogen, hydroxy, alkoxy, aryloxy, oxo, methylene, alkylthio, arylthio, alkanoyl, alkanoyloxy, or halogen; and the broken line in the 15,16-position represents the optional presence of ethylenic unsaturation. The steroids have antiinflammatory activity.

United States patent application Ser. No. 416,181, filed Sept. 9, 1982, discloses androstene-17-dithioketals having the partial structural formula

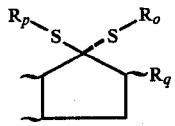

wherein $R_o$ is hydrogen and $R_p$ is alkyl, cycloalkyl, aryl, arylalkyl, alkylthioalkyl, alkoxyalkyl, alkanoyloxyalkyl, aroyloxyalkyl, alkoxycarbonylalkyl, carboxyalkyl, or arylalkyl, or $R_o$ is alkanoyl or aroyl and $R_p$ is alkyl; and $R_q$ is hydrogen, hydroxy, alkoxy, aryloxy, oxo, methylene, alkylthio, arylthio, alkanoyl, alkanoyloxy, or halogen. The steroids are useful intermediates for preparing steroids with antiinflammatory activity.

United States patent application Ser. No. 441,026, filed Nov. 12, 1982, now abandoned discloses androstene-17-dithioketals having the partial structural formula

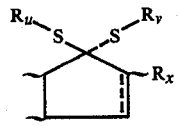

wherein $R_u$ is alkyl, aryl, arylalkyl or cycloalkyl, $R_v$ is alkenyl, substituted alkenyl, alkynyl, substituted alkynyl, mono-, di- or trifluoroalkyl, cyanoalkyl, alkanoylalkyl or wherein n is 1, 2, 3 or 4 and $Y_1$ and $Y_2$ are the same or different and each is hydrogen or alkyl and $R_x$ is hydrogen, hydroxy, alkoxy, aryloxy, oxo (=O), methylene (=$CH_2$), alkylthio, arylthio, alkanoyl, alkanoyloxy, or fluorine, and the broken line in the 15,16-position represents the optional presence of ethylenic unsaturation. The steroids have antiinflammatory activity.

BACKGROUND OF THE INVENTION

United States Pat. No. 4,091,036, issued May 23, 1978, 4,094,840, issued June 13, 1978, 4,133,811, issued Jan. 9, 1979, and 4,146,538, issued Mar. 27, 1979, each discloses androstenes intermediates having the partial structural formula

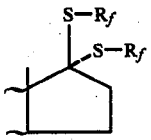

wherein $R_f$ is alkyl or aryl, and both $R_f$ groups are the same.

United States Pat. No. 4,361,559, issued Nov. 30, 1982, discloses androstene-17-dithioketals having the partial structural formula

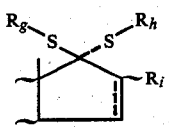

wherein $R_g$ and $R_h$ are the same or different and each is alkyl, cycloalkyl, or aryl; $R_i$ is hydrogen, hydroxy, alkoxy, aryloxy, alkylthio, arylthio,

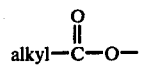

or halogen; and the broken line in the 15,16-position represents the optional presence of ethylenic unsaturation. The steroids have antiinflammatory activity.

BRIEF DESCRIPTION OF THE INVENTION

Steroids having the formula

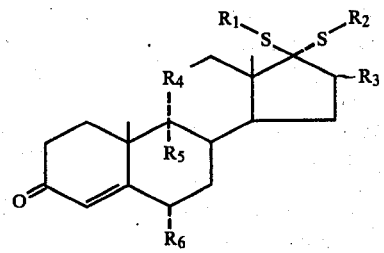

I and the 1,2-dehydro, and 6,7-dehydro derivatives thereof, have topical antiinflammatory activity. In formula I, and throughout the specification, the symbols are as defined below.

One of $R_1$ and $R_2$ is alkyl, aryl, arylalkyl, or cycloalkyl, and the other is alkenyl, substituted alkenyl, alkynyl, substituted alkynyl, mono-, di- or trifluoroalkyl, cyanoalkyl, alkanoylalkyl or wherein n is 1, 2, 3 or 4 and $Y_1$ and $Y_2$ are the same or different and each is hydrogen or alkyl;

$R_3$ is hydrogen, hydroxy, alkoxy, aryloxy, oxo (=O), methylene (=CH$_2$), alkylthio, arylthio, alkanoyl, alkanoyloxy, or fluorine;

$R_4$ is carbonyl, $\beta$-hydroxymethylene or $\beta$-acetyloxymethylene;

$R_5$ is hydrogen or halogen; and $R_6$ is hydrogen, methyl, hydroxy, alkanoyl, alkanoyloxy, or halogen.

The term "aryl", as used throughout the specification either individually or as part of a larger group, refers to phenyl or phenyl substituted with one or two alkyl, alkoxy or halogen groups.

The term "halogen", as used throughout the specification either individually or as part of a larger group, refers to fluorine, chlorine, bromine and iodine.

The terms "alkyl" and "alkoxy", as used throughout the specification either individually or as part of a larger group, refer to groups having 1 to 12 carbon atoms.

The term "cycloalkyl", as used throughout the specification, either individually or as part of a larger group, refers to groups having 3, 4, 5, 6 or 7 carbon atoms.

The term "alkanoyl", as used throughout the specification either individually or as part of a larger group, refers to groups having 2 to 13 carbon atoms.

The terms "alkenyl" and "alkynyl", as used throughout the specification either individually or as part of a larger group, refer to groups having 2 to 13 carbon atoms.

The terms "substituted alkenyl" and "substituted alkynyl", as used throughout the specification either individually or as part of a larger group, refer to alkenyl and alkynyl groups substituted with alkanoyl, alkanoyloxy, alkoxycarbonyl, hydroxy, fluorine, or alkoxy groups.

DETAILED DESCRIPTION OF THE INVENTION

The steroids of formula I, and the 1,2-dehydro, and 6,7-dehydro derivatives thereof, are topical antiinflammatory agents that can be used to treat skin conditions such as dermatitis, psoriasis, sunburn, eczema, neurodermatitis, or anogenital pruritus, and in inhalation therapy for topical treatment of allergy and asthma.

For the treatment of skin conditions, the topical antiinflammatory steroids of this invention may be administered in a conventional pharmaceutical carrier in the form of a cream, ointment, lotion or the like. The steroids will preferably be used in the range of 0.01 to 5.0% by weight of the vehicle, preferably 0.05 to 2.0% by weight of the vehicle.

For the topical treatment of allergy and asthma the topical antiinflammatory steroids of this invention may be administered in the conventional manner, e.g., as solid medicament which has been atomized. United States Pat. No. 3,948,264 and 4,147,166 are exemplary of the literature which describes devices that can be used to administer solid medicaments for inhalation therapy.

The steroids of formula I, and the 1,2-dehydro, and 6,7-dehydro derivatives thereof, wherein $R_1$ is alkyl, aryl, arylalkyl or cycloalkyl, can be prepared utilizing androstenes having the formula

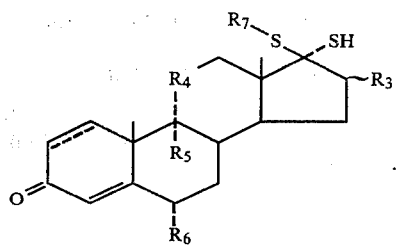

In formula II, and throughout the specification, a broken line in the steroid rings indicates the optional presence of ethylenic unsaturation, and the symbol $R_7$ represents alkyl, aryl, arylalkyl and cycloalkyl.

Reaction of an androstene of formula II with a compound having the formula

yields the corresponding product having the formula

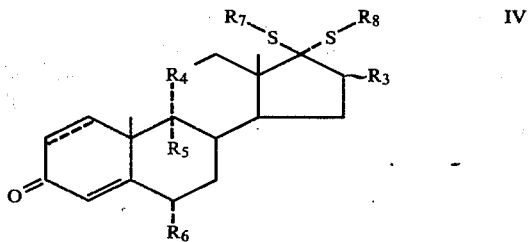

In formulas II, III and IV, Z is a "leaving group" such as a halogen (preferably iodine or bromine) or an alkyl or arylsulfonyl compound (preferably methanesulfonyl or toluenesulfonyl) and $R_8$ is alkenyl, substituted alkenyl, alkynyl, substituted alkynyl, mono-, di- or trifluoroalkyl, cyanoalkyl, alkanoylalkyl or

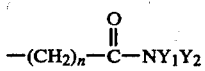

wherein n is 1, 2, 3 or 4 and $Y_1$ and $Y_2$ are the same or different and each is hydrogen or alkyl. The reaction is preferably carried out in the presence of a weak organic or inorganic base.

Alternatively, the steroid of formula I wherein $R_1$ is alkyl, aryl, arylalkyl or cycloalkyl can be prepared utilizing androstenes having the formula

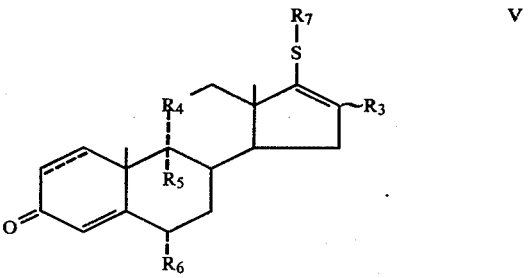

Reaction of a steroid of formula V with a thiol having the formula

yields the corresponding steroid having the formula

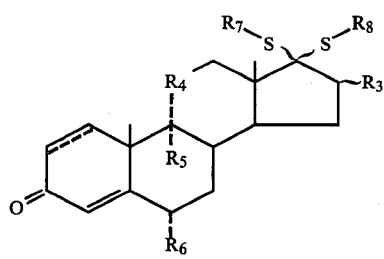    VII as a mixture of isomers. The reaction is run in the presence of a Lewis acid (e.g., boron trifluoride etherate) and will preferably be run at a reduced temperature (i.e., about −20° C. to −100° C.). When the reaction is run at a reduced temperature (i.e., about −20° C. to −100° C.), it is stereospecific, and yields a steroid having the formula

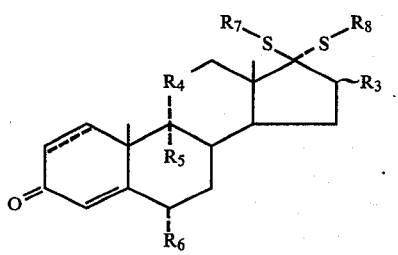    VIII

The steroids of formula I, and the 1,2-dehydro, and 6,7-dehydro derivatives thereof, wherein $R_2$ is alkyl, aryl, arylalkyl or cycloalkyl, can be prepared by alkylation of the corresponding 17-thione having the formula

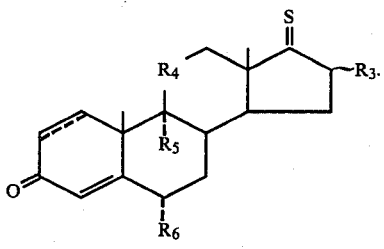    IX

Reaction of a steroid of formula IX with a compound of formula III (i.e., a compound having the formula $R_8$-Z) yields the corresponding steroid having the formula

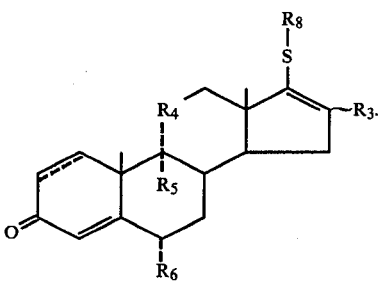    X

Using the procedure described above, a steroid of formula X can be reacted with a thiol having the formula $R_7$—SH    XI in the presence of a Lewis acid to yield the corresponding product having the formula

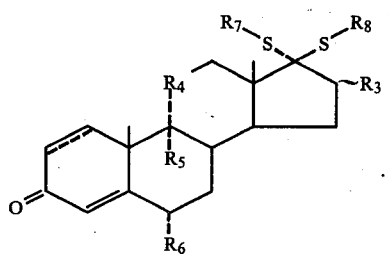    XII

Steroids of formulas II and V can be prepared from the corresponding steroid having the formula

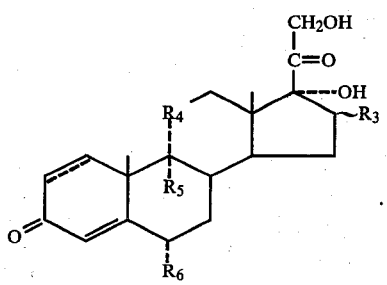    XIII

Treatment of a steroid of formula XIII with sodium bismuthate in the presence of an acid, such as acetic acid, yields the corresponding steroid having the formula

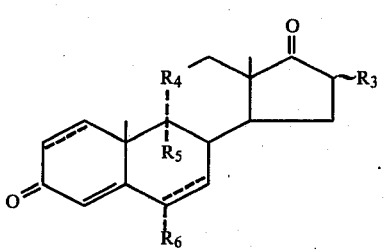    XIV

Alternatively, the androstenes of formula XIV wherein $R_3$ is hydroxy or

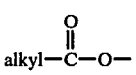

can be prepared by oxidation of the corresponding androstene having the formula

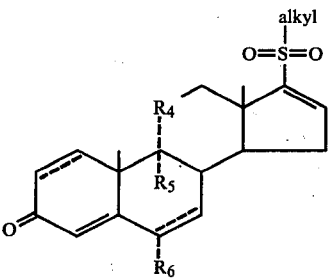    XV with potassium permanganate in the presence of formic acid. The oxidation reaction yields the corresponding 16α(and 16β)-hydroxyandrostene-3,17-dione. These can be acylated using art-recognized procedures to yield the corresponding 16-alkanoyloxy derivative.

Reaction of an androstene of formula XIV with a thiol having the formula

    XVI in the presence of a Lewis acid (e.g., boron trifluoride etherate) yields a steroid having the formula

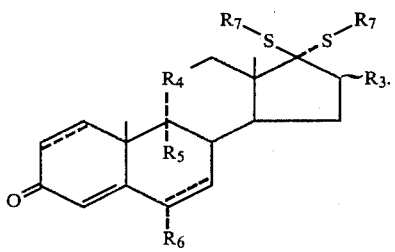    XVII

The reaction can be run in an organic solvent (e.g., a halogenated hydrocarbon), or a mixture of organic solvents. The use of glacial acetic acid as the sole solvent, or in admixture with other solvents, improves yields. Reaction conditions are not critical and the reaction can be conveniently run at room temperature, preferably in an inert atmosphere, (e.g., argon or nitrogen). Better yields can be obtained with relatively short reaction times (less than 1 hour). The addition of a dimethylformamide dialkyl acetal (preferably dimethylformamide dimethyl acetal) also improves yields. Exposure of the crude reaction products, which frequently contain products derived from reaction of the A and B rings with thiols ("over-reacted products") to certain dethiolating agents well known in the art (e.g., methyl iodide in aqueous acetone) also improves the yields.

The steroids of formula XVII can be heated, either neat or in an inert solvent (e.g., diethylbenzene or dichlorobenzene) to yield the desired steroids of formula V. Alternatively, steroids of formula XVII can be oxidized with a peracid (e.g., m-chloroperbenzoic acid) at low temperature (from about −78° C. to 0° C.) and the resulting monosulfoxide heated in an inert low boiling solvent to give the desired steroids of formula V.

Alternatively, compounds of formula V, wherein $R_3$ is chlorine, bromine, alkylthio, or arylthio can be prepared from the corresponding steroid of formula V wherein $R_3$ is hydrogen; i.e., a steroid having the formula

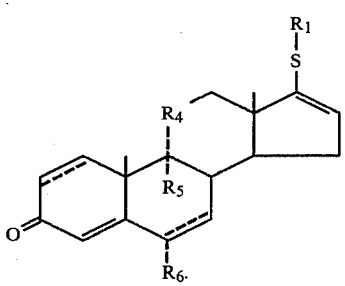    XVIII

Utilizing the procedure described in U.S. Pat. No. 4,265,815, issued May 15, 1981, a steroid of formula V wherein $R_3$ is chlorine or bromine can be obtained by reacting a steroid of formula XVIII with the appropriate N-halosuccinimide, or with chlorine or bromine, preferably in a halogenated hydrocarbon solvent. Steroids of formula V wherein $R_3$ is alkylthio or arylthio can be obtained by reacting the corresponding steroid of formula XVIII with an alkyl or aryl sulfenyl halide, preferably in a halogenated hydrocarbon solvent.

Steroids of formula II can be obtained by reacting a steroid of formula V with hydrogen sulfide. The reaction is run in the presence of a Lewis acid (e.g., boron trifluoride etherate) and will preferably be run at a reduced temperature (i.e., about 0° C. to −20° C.).

The 17-thione androstenes of formula IX are novel compounds, and as such, they form an integral part of this invention, as does the following method for their preparation. Treatment of a hemithioketal of formula II with a tertiary amine base (e.g., triethylamine) or with an alkali metal (preferably potassium or sodium) carbonate yields the corresponding 17-thione androstene of formula IX. The reaction is preferably run in an organic solvent such as dimethylformamide, tetrahydrofuran, or benzene.

As can be seen more clearly in the examples at the end of this specification, it is possible to prepare a 17-thione androstene of formula IX in situ, and utilize it to prepare the corresponding compound of formula X, without first isolating the 17-thione.

In the above-described reactions it may be necessary to protect the 11-hydroxyl group of the steroid reactant. An exemplary family of protecting groups is the acyl family, e.g., alkanoyl groups such as acetyl. Means for protection and deprotection of the 11-hydroxyl group are well-known in the art.

The following examples are specific embodiments of this invention.

EXAMPLE 1

(11β,17β)-9-Fluoro-11-hydroxy-17-(methylthio)-17-[(2,2,2-trifluoroethyl)thio]androsta-1,4-dien-3-one (A)

11β-(Acetyloxy)-9-fluoro-17α-mercapto-17β-(methylthio)androsta-1,4-dien-3-one

A solution of 11β-(acetyloxy)-9-fluoro-17-(methylthio)androsta-1,4,16-triene-3-one (9.0 g) in dry dichloromethane (200 ml) was cooled and stirred in an ice bath and boron trifluoride etherate (6.0 ml) was added. A slow stream of hydrogen sulfide gas was bubbled into the solution for about 3 hours to yield a mixture of the title compound and 11β-(acetyloxy)-9-fluoro-17-thioandrosta-1,4-diene-3-one. The mixture was poured into water and the product was isolated by extraction with chloroform. The chloroform solution was washed with a saturated sodium bicarbonate solution and water, dried (anhydrous magnesium sulfate) and evaporated to give a mixture of the above compounds as a solid. This was chromatographed on silica gel to isolate the title compound, melting point 182°–186° C. and 11β-(acetyloxy)-9-fluoro-17-thioandrosta-1,4-diene-3-one, melting point 157°–158° C.

(B)

(11β,17β)-11-(Acetyloxy)-9-fluoro-17-(methylthio)-17-[(2,2,2-trifluoroethyl)thio]androsta-1,4-dien-3-one To a stirred suspension of potassium carbonate (700 mg) in trifluoroethyl triflate (1.16 g, 5.0 mmole) and dimethylformamide (3.0 ml) was added 11β-(acetyloxy)-9-fluoro-17α-mercapto-17β-(methylthio)androsta- 1,4-diene-3-one (425 mg, 1 mmole) under an argon atmosphere. After 10 minutes, the reaction mixture was partitioned between ethyl acetate and water (50 ml each) and the organic layer separated, washed with water, brine and then dried over anhydrous sodium sulfate before evaporating in vacuo to a crystalline solid. The solid was dissolved in the minimum amount of dichloromethane and adsorbed onto ½ inch of silica gel (in a filter funnel) that had been packed wet with 1:1 ethyl acetate-hexane. Then 3 separate 75 ml volumes of (1:1) ethyl acetate-hexane were passed through the column. Fraction 1 contained all of the product minus baseline impurities and any color observed earlier; the yield was 391 mg with $R_f=0.43$ (1:1) ethyl acetate-hexane and melting point of 182°–184° C.

Microanalysis: Calc'd for $C_{24}H_{30}F_4O_3S_2$: C, 56.90; H, 5.97; S, 12.66; F, 15.0; Found: C, 57.08; H, 5.97; S, 12.43; F, 14.80.

(C)

(11β,17β)-9-Fluoro-11-hydroxy-17-(methylthio)-17-[(2,2,2-trifluoroethyl)thio]androsta-1,4-dien-3-one (11β,17β)-11-(Acetyloxy)-9-fluoro-17-(methylthio)-17-[(2,2,2-trifluoroethyl)thio]-androsta-1,4-dien-3-one (455 mg, 0.898 mmole) was dissolved in tetrahydrofuran (10.0 ml) and methanol (5.0 ml) with magnetic stirring and under an argon atmosphere. A 12% sodium hydroxide solution (0.5 ml) was added and the reaction mixture was stirred for 40 minutes at room temperature. The mixture was then partitioned between ethyl acetate and 5% potassium bisulfate (50 ml each), the organic layer collected, washed with brine, dried over anhydrous sodium sulfate and evaporated in vacuo to a foam. This was recrystallized from ethyl acetate-hexane to give 316 mg of a crystalline solid with melting point 299°–300° C. (dec.).

Microanalysis: Calc'd for $C_{22}H_{28}F_4O_2S_2$: C, 56.88; H, 6.07; F, 16.36; S, 13.80; Found: C, 57.00; H, 6.05; F, 16.10; S, 13.61.

EXAMPLE 2

(11β,17α)-17-[(2-Amino-2-oxoethyl)thio]-9-fluoro-11-hydroxy-17-(methylthio)androsta-1,4-dien-3-one (A)

(11β,17α)-11-(Acetyloxy)-17-[(2-amino-2-oxoethyl)thio]-9-fluoro-17-(methylthio)androsta-1,4-dien-3-one A mixture of 2-chloroacetamide (0.50 g, 5.35 mmole) and powdered potassium carbonate (0.70 g, 5.1 mmole) in dry dimethylformamide (3.0 ml) was treated with 11β-acetyloxy-9-fluoro-17α-mercapto-17β-(methylthio)androsta-1,4-dien-3-one (425 mg, 1.0 mmole) and stirred at room temperature under argon for 1 hour. The mixture was partitioned between ethyl acetate and water (50 ml each), the organic phase washed with water and saturated sodium chloride solution, dried over sodium sulfate and evaporated. The crude product was purified by flash column chromatography on silica gel (35 g) eluting with hexane-ethyl acetate-hexane (3:1) to give the title compound (360 mg), which was recrystallized from ethyl acetate-hexane to give crystals, melting point 194°–195° C.

(B)

(11β,17α)-17-[(2-Amino-2-oxoethyl)thio]-9-fluoro-11-hydroxy-17-(methylthio)androsta-1,4-dien-3-one A solution of (11β,17α)-11-(acetyloxy)-17-[(2-amino-2-oxoethyl)thio]-9-fluoro-17-(methylthio)androsta-1,4-dien-3-one (305 mg, 0.63 mmole) in tetrahydrofuran (8 ml) and methanol (4 ml) was treated with 3 N sodium hydroxide soluion (0.3 ml) and stirred at room temperature under argon for 1.5 hours. The mixture was partitioned between ethyl acetate and 5% potassium bisulfate, the organic phase washed with saturated sodium chloride, dried over sodium sulfate and evaporated to give the title compound (221 mg) as a crystalline solid. Recrystallization from ethyl acetate-hexane gave pure product (212 mg) as granular crystals, melting point 290° C., (dec.).

Anal. Calc'd for $C_{22}H_{30}S_2O_3NF$ (MW 439.62): C, 60.11; H, 6.88; N, 3.19; S, 14.59; F, 4.32; Found: C, 59.98; H, 6.92; N, 3.16; S, 14.55; F, 4.32.

EXAMPLE 3

(11β,17α)-17-[(Cyanomethyl)thio]-9-fluoro-11-hydroxy-17-(methylthio)androsta-1,4-dien-3-one (A)

(11β,17α)-11-(Acetyloxy)-17-[(cyanomethyl)-thio]-9-fluoro-17-(methylthio)androsta-1,4-dien-3-one A mixture of chloroacetonitrile (0.40 ml, 6.32 mmole) and powdered potassium carbonate (0.70 g, 5.1 mmole) in dry dimethylformamide (3.0 ml) was treated with 11β-acetyloxy-9-fluoro-17α-mercapto-17β-(methylthio)androsta-1,4-dien-3-one (425 mg, 1.0 mmole) and stirred at room temperature under argon for 30 minutes. The mixture was partitioned between ethyl acetate and water (50 ml each), the organic phase washed with water and saturated sodium chloride solution, dried over sodium sulfate (anhydrous) and evaporated. The residue was filtered through a pad of silica gel (~5 g) eluting with ethyl acetate-hexane (1:1). Evaporation of the eluent and crystallization from ethyl acetate-hexane gave the pure title compound (436 mg) as crystals, melting point 194°–195° C.

Anal. Calc'd for $C_{24}H_{30}S_2O_3NF$ (MW 463.64): C, 62.17; H, 6.52; N, 3.02; S, 13.83; F, 4.10; Found: C, 62.00; H, 6.59; N, 2.93; S, 13.82; F, 4.09.

(B)

(11β,17α)-17-[(Cyanomethyl)thio]-9-fluoro-11-hydroxy-17-(methylthio)androsta-1,4-dien-3-one A solution of the (11β,17α)-11-(Acetyloxy)-17-[(cyanomethl)thio]-9-fluoro-17-(methylthio)-androsta-1,4-dien-3-one (364 mg, 0.79 mmole) in tetrahydrofuran (10 ml) and methanol (5 ml) was treated with 3 N sodium hydroxide solution (0.4 ml) and stirred at room temperature under argon for 30 minutes. The mixture was partitioned between ethyl acetate and 5% potassium bisulfate, the organic phase washed with saturated sodium chloride, dried over sodium sulfate and evaporated. The crude residue was filtered through a pad of silica gel (~5 g) eluting with ethyl acetate-hexane (1:1). Evaporation of the eluant gave the product (315 mg) a solid. Recrystallization from ethyl acetate-hexane gave pure product (298 mg) as granular crystals, melting point 202° C. (dec.).

Anal. Calc'd for $C_{22}H_{28}S_2O_2NF$ (MW 421.60): C, 62.68; H, 6.69; N, 3.32; S, 15.21; F, 4.51; Found: C, 62.67; H, 6.77; N, 3.20; S, 15.18; F, 4.46.

EXAMPLE 4

(11β,17β)-9-Fluoro-11-hydroxy-17-(methylthio)-17-(2-propynylthio)androsta-1,4-dien-3-one

(A)

(11β,17β)-11-(Acetyloxy)-9-fluoro-17-(methylthio)-17-(2-propynylthio)androsta-1,4-dien-3-one 11β-Acetyloxy-9-fluoro-17α-mercapto-17β-(methylthio)androsta-1,4-dien-3-one (425 mg, 1.0 mmole) was dissolved in dimethylformamide (15.0 ml) with magnetic stirring and under an argon atmosphere. Propargyl bromide (1.7 ml, 19.0 mmol) was then added followed by pulverized potassium carbonate (425 mg). After 45 minutes at room temperature, the reaction mixture was diluted with water, extracted with ethyl acetate (three 100 ml portions), washed with saturated sodium chloride, dried over anhydrous magnesium sulfate and evaporated to a solid weighing 459 mg.

(B)

(11β,17β)-9-Fluoro-11-hydroxy-17-(methylthio)-17-(2-propynylthio)androsta-1,4-dien-3-one (11β,17β)-11-(Acetyloxy)-9-fluoro-17-(methylthio)-17-(2-propynylthio)androsta-1,4-dien-3-one (459 mg) was dissolved in tetrahydrofuran (24.0 ml) and methanol (12.0 ml) with magnetic stirring and under an argon atmosphere. A 12% sodium hydroxide solution (1.5 ml) was then added. After 80 minutes at room temperature the reaction mixture was neutralized with glacial acetic acid, diluted with water and extracted with dichloromethane (three portions). The pooled extracts were washed with a saturated sodium chloride solution, dried over anhydrous magnesium sulfate, filtered and evaporated to a solid (434 mg) which was recrystallized once from ethyl acetate-hexane to give 239 mg of a crystalline compound, melting point of 291°–292° C.

Anal. Calc'd for $C_{23}H_{29}S_2O_2F_1$: C, 65.68; H, 6.95; S, 15.25; F, 4.52; Found: C, 65.54; H, 6.97; S, 15.23; F, 4.50.

EXAMPLE 5

(11β,17β)-9-Fluoro-11-hydroxy-17-(methylthio)-17-(2-butenylthio)androsta-1,4-dien-3-one

(A)

(11β,17β)-11-(Acetyloxy)-9-fluoro-17-(methylthio)-17-(2-butenylthio)androsta-1,4-dien-3-one 11β-Acetyloxy-9-fluoro-17α-mercapto-17β-(methylthio)androsta-1,4-dien-3-one (425 mg, 1.0 mmole) was dissolved in dimethylformamide (15.0 ml) with magnetic stirring and under an argon atmosphere. Crotyl bromide (1.55 ml, 12.0 mmole based on 80% purity) was then added, followed by pulverized potassium carbonate (425 mg). After 40 minutes at room temperature, the reaction mixture was added to water and extracted with three 100 ml portions of ethyl acetate. The extracts were washed with a saturated sodium chloride solution, dried over anhydrous sodium sulfate, and evaporated to a crystalline solid (473 mg).

(B)

(11β,17β)-9-Fluoro-11-hydroxy-17-(methylthio)-17-(2-butenylthio)androsta-1,4-dien-3-one (11β,17β)-11-(Acetyloxy)-9-fluoro-17-(methylthio)-17-(2-butenylthio)androsta-1,4-dien-3-one (473 mg) was dissolved in tetrahydrofuran (20.0 ml) and methanol (10.0 ml) with magnetic stirring under an argon atmosphere. A 3 N sodium hydroxide solution (1.5 ml) was added and the mixture was stirred for 1 hour at room temperature, neutralized with glacial acetic acid, diluted with water and extracted with ethyl acetate (three 75 ml portions). The pooled extracts were washed with a saturated sodium chloride solution, dried over anhydrous sodium sulfate and evaporated to a crystalline solid weighing 487 mg. One recrystallization from ethyl acetate-hexane gave 198 mg of an anayltical specimen, melting point 185°–186° C.

Anal. Calc'd for $C_{24}H_{33}O_2S_2F_1$: C, 66.02; H, 7.62; S, 14.69; F, 4.35; Found: C, 66.05; H, 7.59; S, 14.60; F, 4.32.

EXAMPLE 6

(11β,17β)-17-(Ethylthio)-9-fluoro-11-hydroxy-17-(2-propenylthio)androsta-1,4-dien-3-one

(A)

11β-(Acetyloxy)-9-fluoroandrosta-1,4-dien-3,17-dione

A solution of 20 g of 9-fluoro-11β-hydroxyandrosta-1,4-dien-3,17-dione, 120 ml of glacial acetic acid, 120 ml of acetic anhydride and 5 g of p-toluenesulfonic acid was stirred at room temperature under nitrogen for 20 hours. The resulting solution was quenched with 5 g of sodium acetate. The solvent was partially removed in vacuo at 35°–40° C. and the resultant slurry was diluted with chloroform. The chloroform solution was washed with water, saturated sodium bicarbonate and water, dried over anhydrous sodium sulfate and evaporated in vacuo to give the title compound. This was crystallized from ethyl acetate-hexane to give 20 g of the title compound melting point 177°–178° C.

(B)

11β-(Acetyloxy)-17,17-bis(ethylthio)-9-fluoroandrosta-1,4-dien-3-one

A solution of 20 g (55.5 mmole) of 11β-(acetyloxy)-9-fluoroandrosta-1,4-dien-3,17-dione in 75 ml of dry dichloromethane and 75 ml of glacial acetic acid was stirred with 10 ml of ethanethiol and 2 ml of boron trifluoride etherate at room temperature under nitrogen. After 2.0 hours the resulting solution was diluted with dichloromethane, washed with water, saturated sodium bicarbonate and water, dried over anhydrous sodium sulfate and evaporated in vacuo. The gummy residue was dissolved in 1:1 chloroform-hexane and chromatographed on a 150 g-silica gel column, eluting successively with chloroform-hexane (1:1, 6:4 and 7:3), chloroform, chloroform-ethyl acetate (5:95 and 1:9) and methanol-chloroform (1:9) to give 9.5 g of unreacted 11β-acetyloxy-9-fluoroandrosta-1,4-diene-3,17-dione, 8.2 g of overreacted steroidal product and 5.2 g of the title compound, melting point 148°–150° C.

(C)

11β-(Acetyloxy)-17-(ethylthio)-9-fluoroandrosta-1,4,16-trien-3-one

A suspension of 5.2 g of 11β-(acetyloxy)-17,17-bis(ethylthio)-9-fluoroandrosta-1,4-dien-3-one in 85 ml of dry diethylbenzene was stirred at 180° C. (oil bath temperature) for 1.0 hour; the suspension gradually became a homogeneous solution during the heating. The resulting solution was cooled to 0° C. and the solid that precipitated was filtered and dried in vacuo to give 3.6 g of the title compound, melting point 211°–214° C.

The filtrate was chromatographed on a 30 g-silica gel column, eluting successively with chloroform-hexane (1:1) and chloroform to give 0.4 g more of the title compound.

(D)
(11β,17β)-11-(Acetyloxy)-17-(ethylthio)-9-fluoro-17-(2-propenylthio)androsta-1,4-dien-3-one 11β-(Acetyloxy)-17-(ethylthio)-9-fluoroandrosta-1,4-dien-3-one was dissolved in dry dichloromethane with magnetic stirring under an argon atmosphere. Allyl mercaptan was added and the reaction mixture was cooled to −78° C. (Dry ice/acetone bath) before adding boron trifluoride etherate (0.492 ml, 4.0 mmole). After 15 hours at −78° C., the reaction was quenched at −78° C. with 2 ml of a methanol-sodium hydroxide solution (2 g sodium hydroxide in 30 ml of methanol), diluted with water and extracted with three 50 ml portions of dichloromethane. The pooled extracts were washed with water, dried over anhydrous magnesium sulfate, and evaporated to a crystalline solid weighing 490 mg.

(E)
(11β,17β)-17-(Ethylthio)-9-fluoro-11-hydroxy-17-(2-propenylthio)androsta-1,4-dien-3-one (11β,17β)-11-(Acetyloxy)-17-(ethylthio)-9-fluoro-17-(2-propenylthio)androsta-1,4-dien-3-one (490 mg) was dissolved in tetrahydrofuran (24 ml) and methanol (12.0 ml) with magnetic stirring and under argon atmosphere. A 12% sodium hydroxide solution (1.5 ml) was then added and the mixture was stirred for 1.5 hours at room temperature. The reaction mixture was then neutralized with acetic acid, diluted with water, and extracted with three 50 ml portions of dichloromethane. The pooled extracts were washed with water, dried over anhydrous magnesium sulfate, filtered, and evaporated to a crystalline solid 436 mg which was recrystallized once from ethyl acetate-hexane to give 326 mg of an analytical specimen, melting point of 194°–196° C.

Anal. calc'd for $C_{24}H_{33}S_2O_2F$: C, 66.02; H, 7.62; S, 14.62; F, 4.35; Found: C, 65.81; H, 7.62; S, 14.51; F, 4.30.

EXAMPLE 7
(11β,17β)-9-Fluoro-11-hydroxy-17-(methylthio)-17-(2-propenylthio)androsta-1,4-dien-3-one

(A)
11β-(Acetyloxy)-17,17-bis(methylthio)-9-fluoroandrosta-1,4-dien-3-one

To a solution of 11β-(acetyloxy)-9-fluoroandrosta-1,4-dien-3-one (5.0 g) in a mixture of acetic acid (25 ml) and dichloromethane (25 ml) containing methanethiol (2.5 ml) was added distilled boron trifluoride etherate (0.5 ml) and the mixture was stirred for one hour. It was then added to water (150 ml) and was extracted with chloroform. The chloroform solution was washed with water, saturated sodium bicarbonate solution and water, dried (anhydrous magnesium sulfate) and evaporated. The residue was absorbed on a column of silica gel (30 g). Successive elutions of the column with chloroform-hexane (4:1), chloroform and chloroform-ethyl acetate (95:5 and 9:1) afforded overreacted steroid containing thiol-derived impurities (3.0 g), the title compound (1.7 g) and unreacted starting material. Crystallization of the 1.7 g material from acetone-hexane gave 1.2 g of material, melting point 224°–225° C., (dec.).

(B)
11β-(Acetyloxy)-9-fluoro-17-(methylthio)-androsta-1,4,16-triene-3-one

11β-(Acetyloxy)-17,17-bis(methylthio)-9-fluoroandrosta-1,4-dien-3-one (1.1 g) was suspended in dry diethylbenzene (30 ml). After refluxing for twenty minutes, the solution was cooled, poured on a column of silica gel (15 g) and the column was eluted successively with chloroform-hexane (7:3), chloroform and chloroform-ethyl acetate (95:5) to isolate the title compound (900 mg) and 11β-acetyloxy-9-fluoroandrosta-1,4-diene-3,17-dione (120 mg). Crystallization of the 900 mg of material from ethyl acetate-hexane gave 800 mg of material, melting point 202°–203° C.

(C)
(11β,17β)-9-Fluoro-11-hydroxy-17-(methylthio)-17-(2-propenylthio)androsta-1,4-dien-3-one 11β-(Acetyloxy)-9-fluoro-17-(methylthio)-androsta-1,4,16-triene-3-one (2.4 g, 6.0 mmole) was dissolved in dry dichloromethane (75.0 ml) with magnetic stirring and under a nitrogen atmosphere. Once the steroid had dissolved, allyl mercaptan (3.0 ml) was added, the mixture cooled to −78° C. via a Dry ice-acetone bath and treated with boron trifluoride etherate (2.25 ml, 18.0 mmole). After 6.5 hours at −78° C., an additional 0.75 ml (6.0 mmole) of boron trifluoride etherate was added. After a total of 23 hours at −78° C., the reaction mixture was quenched with 200 ml of an ice cold 10% potassium hydroxide solution and chloroform extracted (four 100 ml portions). The extracts were dried over anhydrous magnesium sulfate and evaporated to a solid residue (2.6 g).

(D)
(11β,17β)-9-Fluoro-11-hydroxy-17-(methylthio)-17-(2-propenylthio)androsta-1,4-dien-3-one (11β,17β)-9-Fluoro-11-hydroxy-17-(methylthio)-17-(2-propenylthio)androsta-1,4-dien-3-one (2.6 g) was dissolved in tetrahydrofuran (72.0 ml) and methanol (36.0 ml) with magnetic stirring under a nitrogen atmosphere. A 12% sodium hydroxide solution (9.0 ml) was added and after 1.5 hours at room temperature, the mixture was quenched by pouring it into 200 ml of water. The mixture was then extracted with chloroform (three 180 ml portions). The extracts were washed with water, dried over anhydrous magnesium sulfate, filtered, and evaporated to a solid which was taken up in 50 ml of boiling ethyl acetate and recrystallized. One recrystallization yielded 1.24 g of a crystalline solid. A second recrystallization of the material from the mother liquor with ethyl acetate yielded another 607 mg. The crystals were combined to yield 1.847 g of the desired product, melting point 283°–285° C.

Anal. Calc'd for $C_{23}H_{31}FO_2S_2$: C, 65.37; H, 7.39; F, 4.50; S, 15.17; Found: C, 65.65; H, 7.40; F, 4.50; S, 15.19.

EXAMPLE 8
(11β,17α)-9-Fluoro-17-[(2-fluoroethyl)thio]-11-hydroxy-17-(methylthio)androsta-1,4-dien-3-one

(A)
(11β,17α)-11-(Acetyloxy)-9-fluoro-17-[(2-fluoroethyl)-thio]-17-(methylthio)androsta-1,4-dien-3-one A mixture of 2-bromofluoroethane (0.65 g, 5.1 mmole) and powdered potassium carbonate (0.70 g, 5.1 mmole) in dry dimethylformamide (3.0 ml) was treated with 11β-(acetyloxy)-9-fluoro-17α-mercapto-17β-(methylthio)androsta-1,4-dien-3-one (425 mg, 1.0 mmole) and stirred at room temperature under argon for 45 minutes. The mixture was partitioned between ethyl acetate and water (50 ml each), and the organic phase was washed with water and saturated sodium chloride solution, dried over sodium sulfate (anhydrous) and evaporated. The residue was purified by flash chromatography on silica gel (35 g) eluting with ethyl acetate-hexane (1:2) to give the title compound (420 mg). The product was recrystallized from ethyl acetate-hexane to give pure product (404mg) as fluffy crystals, melting point 185°–186° C.

(B)
(11β,17α)-9-Fluoro-17-[(2-fluoroethyl)thio]-11-hydroxy-17-(methylthio)androsta-1,4-dien-3-one A solution of (11β,17α)-11-(acetyloxy)-9-fluoro-17-[(2-fluoroethyl)thio]-17-(methylthio)-androsta-1,4-dien-3-one in tetrahydrofuran (10 ml)-methanol (5 ml) was treated with 3 N sodium hydroxide solution (0.5 ml, 1.5 mmole) and stirred at room temperature under argon for 30 minutes. The mixture was partitioned between ethyl acetate and 5% potassium bisulfate, and the organic phase was washed with saturated sodium chloride, dried over sodium sulfate and evaporated. The crude product (306 mg) was recrystallized from ethyl acetate-hexane to give the title compound (300 mg) as white granular crystals, melting point 190°–191° C. (dec.).

Anal. Calc'd for $C_{22}H_{30}S_2O_2F_2$: C, 61.65; H, 7.06; S, 14.96; F, 8.86; Found: C, 61.62; H, 7.00; S, 14.99; F, 8.80.

EXAMPLE 9

(11β,17α)-17-(Ethylthio)-9-fluoro-11-hydroxy-17-[(2,2,2-trifluoroethyl)thio]androsta-1,4-dien-3-one (A) 11β-(Acetyloxy)-9-fluoro-17-[(2,2,2-trifluoroethylthio]androsta-1,4,16-trien-3-one 11β-(Acetyloxy)-9-fluoro-17α-mercapto-17β-(methylthio)androsta-1,4-dien-3-one (427 mg, 1.0 mmole; see example 1A) was added to a stirred suspension of pulverized potassium carbonate (700 mg) in dimethylformamide (5.0 ml); the solution immediately turned yellow. Trifluoroethyl iodide (0.30 ml, 30 mmole, 0.63 g) was then added discharging the yellow color. After 15 minutes at room temperature, the reaction mixture was partitioned between water and ethyl acetate and the organic layer separated, washed with brine, and evaporated in vacuo to a crystalline solid. One recrystallization from ethyl acetate/hexane gave 326 mg of the desired product as a white crystalline solid with a melting point of 194°–196° C.

Anal.: Calc'd for $C_{23}H_{25}F_4O_3S$: C, 60.38; H, 5.51; S, 7.01; F, 16.61; Found: C, 60.18; H, 5.83; S, 7.26; F, 16.50.

(B)
(11β,17α)-11-(Acetyloxy)-17-(ethylthio)-9-fluoro-17-[(2,2,2-trifluoroethyl)thio]androsta-1,4-dien-3-one To a magnetically stirred solution of 11β-(Acetyloxy)-9-fluoro-17-[(2,2,2-trifluoroethyl)thio]androsta-1,4,16-trien-3-one (300 mg, 0.66 mmole) in dry dichloromethane (10.0 ml) under argon was added ethyl mercaptan (0.166 g, 0.2 ml, 2.64 mmole). The reaction mixture was cooled to −78° C. (Dry ice/acetone) and treated with boron trifluoride etherate (0.325 ml, 2.64 mmole). After 24.0 hours at −78° C., the mixture was warmed to −27° C. and maintained at this temperature for 48.0 hours. The reaction mixture was quenched by treatment with 5.0 ml of a sodium hydroxide/methanol solution (2 g sodium hydroxide in 30 ml of methanol) and partitioned between ethyl acetate and water. The separated organic layer was washed with brine, dried over anhydrous sodium sulfate and evaporated in vacuo to a clear oil (343 mg). One recrystallization from ethyl acetate/hexane gave the desired compound as long white crystals with a melting point of 188°–190° C. (282 mg).

Anal.: Calc'd for $C_{25}H_{32}F_4O_3S_2$: C, 57.67; H, 6.20; S, 12.32; F, 14.69; Found: C, 57.79; H, 6.17; S, 12.25; F, 14.46.

(C)
(11β,17α)-17-(Ethylthio)-9-fluoro-11-hydroxy-17-[(2,2,2-trifluoroethyl)thio]androsta-1,4-dien-3-one To a stirred solution of (11β,17α)-11-(acetyloxy)-17-(ethylthio)-9-fluoro-17-[(2,2,2-trifluoroethyl)thio]androsta-1,4-dien-3-one (251 mg, 0.482 mmole) in 5.0 ml of tetrahydrofuran and 5.0 ml of methanol under argon was added 0.25 ml of a 12% sodium hydroxide solution. After 2 hours at room temperature, the reaction mixture was neutralized to litmus with a few ml of glacial acetic acid and then partitioned between ethyl acetate and water. The organic layer was washed with brine, dried over anhydrous sodium sulfate and evaporated in vacuo to give a white foam (233 mg). One recrystallization from ethyl acetate/hexane gave 206 mg of the title compound as white granular crystals with a melting point of 230°–232° C.

Anal. Calc'd for $C_{23}H_{30}F_4O_2S_2$: C, 57.72; H, 6.34; F, 15.88; S, 13.40; Found: C, 58.03; H, 6.23; F, 15.59; S, 13.39.

EXAMPLE 10

(11β,17α)-17-(Ethylthio)-9-fluoro-17-[(2-fluoroethyl)thio]-11-hydroxyandrosta-1,4-dien-3-one (A)
11β-(Acetyloxy)-9-fluoro-17-thioandrosta-1,4-dien-3-one A solution of 11β-(acetyloxy)-9-fluoro-17α-mercapto-17β-(methylthio)androsta-1,4-dien-3-one (2.0 g, 4.72 mmole; see example 1A) and triethylamine (2.0, 14.6 mmole) in dry tetrahydrofuran (24 ml) was refluxed under argon for 22 hours. The mixture was evaporated to dryness to give 1.87 g of the crude title compound. Crystallization from ethyl acetate/hexane gave pure product, melting point 151°–153° C.

(B)
11β-(Acetyloxy)-9-fluoro-17-[2-fluoroethyl)thio]androsta-1,4,16-trien-3-one

A solution of 11β-(acetyloxy)-9-fluoro-17-thioandrosta-1,4-dien-3-one (1.87 g, 4.7 mmole) in a mixture of dry tetrahydrofuran (10 ml) and dimethylformamde (5 ml) was treated with triethylamine (2.0 ml) and 2-bromofluoroethane (2.0 ml, 24 mmole) and stirred at room temperature under argon for 6 hours. The mixture was partitioned between ethyl acetate/5% potassium bisulfate, the organic phase washed with water and saturated sodium chloride, dried over sodium sulfate and evaporated. The residue was filtered through a pad of silica gel eluting with ethyl acetate/dichloromethane (1:9). Evaporation of the eluate and recrystallization of the residue from ethyl acetate/hexane gave the title compound (1.60 g) as fluffy white cyrstals, melting point 198°–199° C.

Anal: Calc'd. for $C_{23}H_{28}SO_3F_2$ (MW 422.54): C, 65.38; H, 6.68; S, 7.59; F, 8.99; Found: C, 65.35; H, 6.70; S, 7.59; F, 8.99.

(C)
(11β,17α)-11-(Acetyloxy)-17-(ethylthio)-9-fluoro-17-[(2-fluoroethyl)thio]androsta-1,4-dien-3-one A solution of 11β-(acetyloxy)-9-fluoro-17-[(2-fluoroethyl)thio]androsta-1,4,16-trien-3-one (350 mg, 0.83 mmole) and ethanethiol (1.5 ml, 20 mmole) in dry dichloromethane (15.0 ml) at −78° C. (Dry ice-acetone bath) under argon, was treated with boron trifluoride etherate (0.4 ml, 3.25 mmole) and kept at −78° C. to −70° C. for 18 hours. The reaction was then quenched by treatment with methanolic sodium hydroxide (1.5 ml of a solution prepared by dissolving 1.0 g sodium hydroxide in 15.0 methanol) at −78° C. and immediately partitioned between dichloromethane and 5% potassium bisulfate. The organic phase was washed with water, dried over sodium sulfate and evaporated. Recrystallization of the residue from ethyl acetate/hexane gave the title compound (340 mg) as white needles, melting point 152°–153° C.

Anal. Calc'd for $C_{25}H_{34}S_2O_3F$ (MW 484.67): C,61.95; H, 7.07; S, 13.23; F, 7.84; Found: C, 62.10; H, 7.07; S, 13.15; F, 7.81.

(D)
(11β,17α)-17-(Ethylthio)-9-fluoro-17-[(2-fluoroethyl)thio]-11-hydroxyandrosta-1,4-dien-3-one A solution of (11β,17α)-11-(acetyloxy)-17-(ethylthio)-9-fluoro-17-[(2-fluoroethyl)thio]androsta-1,4-dien-3-one (300 mg, 0.62 mmole) in tetrahydrofuran (8.0 ml) methanol (4.0 ml) under argon was treated with a 3 N sodium hydroxide solution (0.3 ml, 0.9 mmole) and stirred at room temperature for 1 hour. The mixture was partitioned between ethyl acetate and 5% potassium bisulfate and the organic phase washed with saturated sodium chloride, dried over sodium sulfate and evaporated to give the crude product, (263 mg) as a white solid. Recrystallization from ethyl acetate/hexane gave pure product (251.5 mg) as white plates, melting point 202°–203° C., (dec).

Anal. Calc'd for $C_{23}H_{32}S_2O_2F_2$ (MW 442.63) C, 62.41; H, 7.29, S, 14.49; F, 8.58 Found: C, 62.64; H, 7.29; S, 14.42; F, 8.57.

EXAMPLE 11
(11β,17β)-9-fluoro-17-[(2-fluoroethyl)thio]-11-hydroxy-17-propylthioandrosta-1,4-dien-3-one A solution of 11β-(Acetyloxy)-9-fluoro-17-[(2-fluoroethyl)thio]androsta-1,4,16-trien-3-one (400 mg, 0.95 mmole; see example 10B) and propanethiol (1.5 ml) in dry dichloromethane (15.0 ml) at −78° C. (Dry ice-acetone bath) under argon, was treated with boron trifluoride etherate (0.45 ml, 3.6 mmole) and kept at −78° C. to −70° C. for 18 hours. The reaction was then quenched by treatment with methanolic sodium hydroxide (1.5 ml of a solution prepared by dissolving 1.0 g of sodium hydroxide in 15.0 ml of methanol) at −78° C. and immediately partitioned between dichloromethane and 5% potassium bisulfate. The organic phase was washed with water, dried over sodium sulfate and evaporated. The residue was taken up in tetrahydrofuran (10.0 ml) and methanol (5.0 ml) and treated with a 3 N sodium hydroxide solution (0.5 ml, 1.5 mmole) and stirred at room temperature under argon for 1 hour. The mixture was partitioned between ethyl acetate and 5% potassium bisulfate and the organic phase washed with saturated sodium chloride, dried over sodium sulfate and evaporated. The crude product was recrystallized from ethyl acetate/hexane to give the title compound (387 mg) as white plates, melting point 215°–217° C. (dec.).

What is claimed is:

1. A steroid having the formula

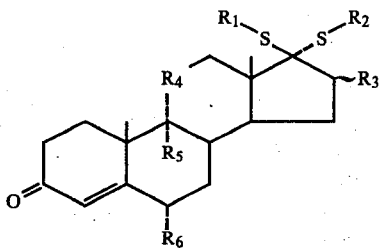

or a 1,2-dehydro, or 6,7-dehydro derivatives thereof, wherein
one of $R_1$ and $R_2$ is alkyl, aryl, arylalkyl, or cycloalkyl, and the other is alkenyl, substituted alkenyl, alkynyl, substituted alkynyl, mono-, di- or trifluoroalkyl, cyanoalkyl, alkanoylalkyl or

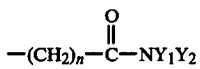

wherein n is 1, 2, 3 or 4 and $Y_1$ and $Y_2$ are the same or different and each is hydrogen or alkyl;
$R_3$ is hydrogen, hydroxy, alkoxy, aryloxy, oxo, methylene, alkylthio, arylthio, alkanoyl, alkanoyloxy, or fluorine;
$R_4$ is carbonyl, β-hydroxymethylene or β-acetyloxymethylene;
$R_5$ is hydrogen or halogen; and
$R_6$ is hydrogen, methyl, hydroxy, alkanoyl, alkanoyloxy or halogen.

2. A steroid in accordance with claim 1 wherein $R_1$ is alkyl, aryl, arylalkyl or cycloalkyl.

3. A steroid in accordance with claim 1 wherein $R_2$ is alkyl, aryl, arylalkyl or cycloalkyl.

4. A steroid in accordance with claim 1 wherein $R_1$ is methyl or ethyl.

5. A steroid in accordance with claim 1 wherein $R_2$ is methyl or ethyl.

6. A steroid in accordance with claim 1 wherein $R_1$ is mono-, di- or trifluoroalkyl.

7. A steroid in accordance with claim 1 wherein $R_2$ is mono-, di- or trifluoroalkyl.

8. A steroid in accordance with claim 1 wherein $R_4$ is β-hydroxymethylene.

9. A steroid in accordance with claim 1 wherein $R_5$ is fluorine.

10. A steroid in accordance with claim 1 wherein $R_6$ is hydrogen.

11. A steroid in accordance with claim 1 wherein $R_4$ is β-hydroxymethylene, $R_5$ is fluorine and $R_6$ is hydrogen.

12. The steroid in accordance with claim 1 (11β,17β)-9-fluoro-11-hydroxy-17-(methylthio)-17-[(2,2,2-trifluoroethyl)thio]androsta-1,4-dien-3-one.

13. the steroid in accordance with claim 1 (11β,17α)-17-[(2-amino-2-oxoethyl)thio]-9-fluoro-11-hydroxy-17-(methylthio)androsta-1,4-dien-3-one.

14. The steroid in accordance with claim 1 (11β,17α)-17-[(cyanomethyl)thio]-9-fluoro-11-hydroxy-17-(methylthio)androsta-1,4-dien-3-one.

15. The steroid in accordance with claim 1 (11β,17β)-9-fluoro-11-hydroxy-17-(methylthio)-17-(2-propynylthio)androsta-1,4-dien-3-one.

16. The steroid in accordance with claim 1 (11β,17β)-9-fluoro-11-hydroxy-17-(methylthio)-17-(2-butenylthio)androsta-1,4-dien-3-one.

17. The steroid in accordance with claim 1 (11β,17β)-17-(ethylthio)-9-fluoro-11-hydroxy-17-(2-propenylthio)androsta-1,4-dien-3-one.

18. The steroid in accordance with claim 1 (11β,17β)-9-fluoro-11-hydroxy-17-(methylthio)-17-(2-propenylthio)androsta-1,4-dien-3-one.

19. The steroid in accordance with claim 1 (11β,17α)-17-(ethylthio)-9-fluoro-11-hydroxy-17-[(2,2,2-trifluoroethyl)thio]androsta-1,4-dien-3-one.

20. The steroid in accordance with claim 1 (11β,17α)-17-(ethylthio)-9-fluoro-17-[(2-fluoroethyl)thio]-11-hydroxyandrosta-1,4-dien-3-one.

21. The steroid in accordance with claim 1 (11β,17β)-9-fluoro-17-[(2-fluoroethyl)thio]-11-hydroxy-17-propylthioandrosta-1,4-dien-3-one.

22. A steroid having the formula

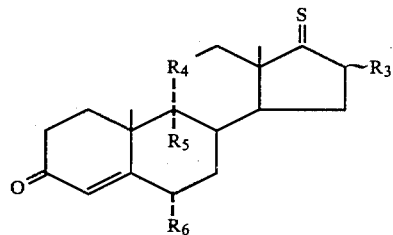

or a 1,2-dehydro or 6,7-dehydro derivatives thereof, wherein
- $R_3$ is hydrogen, hydroxy, alkoxy, aryloxy, oxo, methylene, alkylthio, arylthio, alkanoyl, alkanoyloxy, or fluorine;
- $R_4$ is carbonyl, β-hydroxymethylene or β-acetyloxymethylene;
- $R_5$ is hydrogen or halogen; and
- $R_6$ is hydrogen, methyl, hydroxy, alkanoyl, alkanoyloxy or halogen.

23. A method for preparing a steroid having the formula

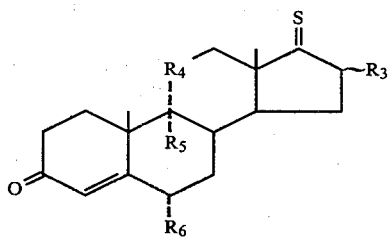

or a 1,2-dehydro or 6,7-dehydro derivative thereof, which comprises treating a corresponding steroid having the formula

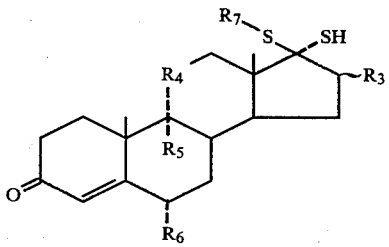

or 1,2-dehydro or 6,7-dehydro derivative thereof, with a tertiary amine base or an alkali metal carbonate, wherein
- $R_3$ is hydrogen, hydroxy, alkoxy, aryloxy, oxo, methylene, alkylthio, arylthio, alkanoyl, alkanoyloxy, or fluorine;
- $R_4$ is carbonyl, β-hydroxymethylene or β-acetyloxymethylene;
- $R_5$ is hydrogen or halogen;
- $R_6$ is hydrogen, methyl, hydroxy, alkanoyl, alkanoyloxy or halogen; and
- $R_7$ is alkyl, aryl, arylalkyl or cycloalkyl.

* * * * *

UNITED STATES PATENT AND TRADEMARK OFFICE
CERTIFICATE OF CORRECTION

PATENT NO. : 4,427,592

DATED : January 24, 1984

INVENTOR(S) : Ravi K. Varma et al.

It is certified that error appears in the above—identified patent and that said Letters Patent is hereby corrected as shown below:

In the Abstract, correct the structure to read as follows:

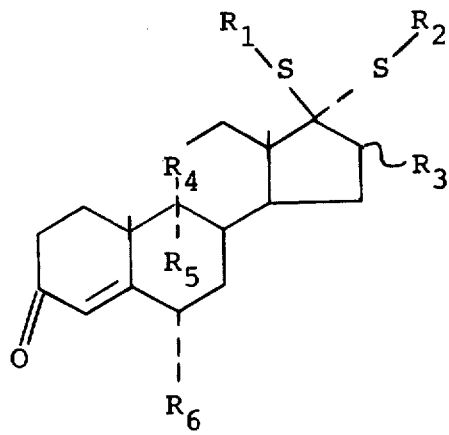

In column 10, line 50, "cyanomethl" should be --cyanomethyl--.

In column 13, line 34 "436 mg) should be --(436 mg)--.

In column 18, line 63, claim 13, "the" should be --The--.

Signed and Sealed this

Third Day of July 1984

[SEAL]

Attest:

GERALD J. MOSSINGHOFF

Attesting Officer    Commissioner of Patents and Trademarks